US011318181B2

(12) United States Patent
Bränning et al.

(10) Patent No.: US 11,318,181 B2
(45) Date of Patent: May 3, 2022

(54) NON-FERMENTED COMPOSITIONS COMPRISING A CEREAL BASED FRACTION AND A PROBIOTIC AND USES THEREOF (71) Applicant: Probi AB, Lund (SE)

(72) Inventors: Camilla Bränning, Lund (SE); Margareta Nyman, Lund (SE)

(73) Assignee: PROBI AB, Lund (SE)

(*) Notice: Subject to any disclaimer, the term of this patent is extended or adjusted under 35 U.S.C. 154(b) by 252 days.

(21) Appl. No.: 16/282,059

(22) Filed: Feb. 21, 2019

(65) Prior Publication Data
US 2019/0201473 A1 Jul. 4, 2019

Related U.S. Application Data (62) Division of application No. 13/513,290, filed as application No. PCT/SE2010/051464 on Dec. 22, 2010, now abandoned.

(30) Foreign Application Priority Data

Dec. 22, 2009 (SE) .................... 0951011-6

(51) Int. Cl.
A61K 36/899 (2006.01)
A61K 35/74 (2015.01)
A23L 7/10 (2016.01)
A23L 7/104 (2016.01)
A23L 7/117 (2016.01)
A23L 7/20 (2016.01)
A23L 33/135 (2016.01)

(52) U.S. Cl.
CPC ............ A61K 36/899 (2013.01); A23L 7/104 (2016.08); A23L 7/115 (2016.08); A23L 7/117 (2016.08); A23L 7/20 (2016.08); A23L 33/135 (2016.08); A61K 35/74 (2013.01); A23V 2002/00 (2013.01); A23Y 2220/67 (2013.01)

(58) Field of Classification Search
CPC ....... A61K 36/899; A61K 35/74; A23L 7/104; A23L 7/117; A23L 7/20; A23L 7/115; A23L 33/135; A23V 2002/00; A23Y 2220/67
USPC ...................................................... 424/93.45
See application file for complete search history.

(56) References Cited

U.S. PATENT DOCUMENTS

| 5,260,092 A | 11/1993 | Gannon |
| 5,587,314 A | 12/1996 | Bengmark et al. |
| 6,241,983 B1 | 6/2001 | Paul et al. |
| 6,348,221 B1 | 2/2002 | Kanauchi et al. |
| 2002/0146399 A1 | 10/2002 | Raczek |
| 2007/0231311 A1 | 10/2007 | Kroening et al. |
| 2008/0193485 A1 | 8/2008 | Gorbach et al. |
| 2008/0311097 A1 | 12/2008 | Israelsen |
| 2009/0130249 A1 | 5/2009 | Conard et al. |
| 2011/0262571 A1 | 10/2011 | Kanauchi et al. |

FOREIGN PATENT DOCUMENTS

| EP | 0904784 A1 | 3/1999 |
| EP | 1769801 A1 | 4/2007 |
| JP | H01206958 A | 8/1989 |
| JP | H06501624 A | 2/1994 |
| JP | 2001-506129 A | 5/2001 |
| JP | 2002-119276 A | 4/2002 |
| JP | 2004-520276 A | 7/2004 |
| JP | 2006-069993 A | 3/2006 |
| JP | 2006-521817 A | 9/2006 |
| RU | 2284703 C1 | 10/2006 |
| WO | 1993/001823 A1 | 2/1993 |
| WO | 97/034591 A1 | 9/1997 |
| WO | 1998/026787 A1 | 6/1998 |
| WO | 00/33854 A1 | 6/2000 |
| WO | 2002/038165 A1 | 5/2002 |
| WO | 03/088984 A1 | 10/2003 |
| WO | 2004/022727 A1 | 3/2004 |
| WO | 2004/087893 A9 | 3/2006 |
| WO | 2006/041930 A2 | 4/2006 |
| WO | 2006/088923 A2 | 8/2006 |

OTHER PUBLICATIONS

Niedzielin, K., et al. (2001), "A controlled, double-blind, randomized study on the efficacy of Lactobacillus plantarum 299V in patients with irritable bowel syndrome", European Journal of Gastroenterology & Hepatology, 13(10): 1143-1147.
Nilsson et al., "Carboxylic Acids in the Hidgut of Rats Fed Highly Soluble Inulin and Bifidobacterium Lactis (Bb-12), Lactobacillus Salivarius (UCC500) or Lactobacillus Rhamnosus (GG)", Scandinavian Journal of Food and Nutrition 2007:51 (1): 13-21.
Nilsson, U., et al., "Dietary supplementation with -glucan enriched oat bran increases faecal concentration of carboxylic acids in healthy subjects," European Journal of Chemical Nutrition, 62:978-984, (2008).
Nobaek, S., et al. (2000), "Alteration of Intestinal Microflora Is Associated With Reduction in Abdominal Bloating and Pain in Patients With Irritable Bowel Syndrome", The American Journal of Gastroenterology, 95(5): 1231-1238.
Office Action dated Sep. 17, 2013 issued in U.S. Appl. No. 13/513,290.
Office Action dated Apr. 2, 2018 issued in U.S. Appl. No. 13/513,290.
Office Action dated Dec. 2, 2014 issued in Japanese Application No. 2012-545906—English Translation Only.

(Continued)

Primary Examiner — Jennifer M. H. Tichy
(74) Attorney, Agent, or Firm — Harness Dickey & Pierce P.L.C.

(57) ABSTRACT

The present invention relates to a non-fermented composition having the ability to increase the formation of butyric acid in the colon and comprising at least one cereal based fraction and at least one isolated probiotic strain of *Lactobacillus* as well as the use of said non-fermented composition as a synbiotic and for treatment of the metabolic syndrome, ulcerative colitis, Crohns disease, Irritable bowel syndrome (IBS), or Inflammatory bowel disease (IBD). The non-fermented composition of the invention is useful for the maintenance of a healthy gut-mucosa and/or for the provision of an increased barrier function of the gut-mucosa.

21 Claims, 1 Drawing Sheet (56) References Cited

OTHER PUBLICATIONS

Office Action dated Sep. 2, 2016 issued in U.S. Appl. No. 13/513,290.
Office Action dated Mar. 20, 2013 issued in U.S. Appl. No. 13/513,290.
Office Action dated Dec. 21, 2018 issued in U.S. Appl. No. 13/513,290.
Office Action dated Nov. 21, 2017 issued in U.S. Appl. No. 13/513,290.
Office Action dated Jan. 29, 2016 issued in U.S. Appl. No. 13/513,290.
Office Action dated Jun. 3, 2014 issued in U.S. Appl. No. 13/513,290.
Office Action dated Mar. 30, 2017 issued in U.S. Appl. No. 13/513,290.
Office Action dated Dec. 5, 2014 issued in Russian Application No. 2012125192/10(038587)—English Translation Only.
Office Action dated Feb. 6, 2015 issued in U.S. Appl. No. 13/513,290.
Osteoporosis [http://probi.se/sites/ali/files/attachment_fiies/osteoporosis_nov_2015.pdf].
Plessas, S., et al. (2007) "Immobilization of kefir and lactobacillus easel on brewery spent grains for use in sourdough wheat bread making" Food Chemistry, vol. 105, pp. 187-194.
Rask, C., et al. (2013), "Differential effect on cell-mediated immunity in human volunteers after intake of different lavtobacilli". Clinical & Experimental Immunology, 172(2): 321-332.
Sieo, C., et al. (2005), "Influence of b-Glucanase-Producing Lactobacillus Strains on Intestinal Characteristics and Feed Passage Rate of Broiler Chickens", Poultry Science, 84: 734-741.
Stress and recovery [http://probi.se/sites/all/files/attachment_files/stress_and_recovery_nov_2015_0.pdf].
Van Immerseel, F., et al., "Butyric acid-producing anaerobic bacteria as a novel probiotic treatment approach for inflammatory bowel disease," Journal of Medical Microbiology, 141-143, (2010).
Vasquez, A., et al. (2005), "Oral administration of Lactobacillus and Bifidobacterium strains of intestinal and vaginal origin to healthy human females: Re-isolation from faeces and vagina", Microbial Ecology in Health and Disease, 17(1): 15-20.
Zaleski, A., et al., "Butyric acid in irritable bowel syndrome," Prz Gastroenterol, 8(6):350-353, (2013).
Ahrné, S., et al. (1998), "The normal Lactobacillus flora of healthy human rectal and oral mucosa", Journal of Applied Microbiology, 85(1):88-94.
Alderberth, A., et al. (1996), "A Mannose-Specific Adherence Mechanism in Lactobacillus plantarum Conferring Binding to the Human Colonic Cell Line HT-29", Applied and Environmental Microbiology 62(7): 2244-2251.
Antonsson, M., et al. (2001), "A comparison between the microflora of Herrgård cheese from three different dairies", International Dairy Journal, 11: 285-291.
Baah, J., et al. (2009) "Impact of a mixed culture of Lactobacillus casei and L. lactis on in vitro ruminal fermentation and the growth of feedlot steers fed barley-based diets", Can. J. Anim. Sci., 89:263-271.
Bengmark, S., et al. (1996), "Nutritional Support to Prevent and Treat. Multiple Organ Failure", World J. Surg. 20(4): 474-481.
Berggren, A., et al. (2011), "Randomised, double-blind and placebo-controlled study using new probiotic lactobacilli for strengthening the body immune defence against viral infections", Eur J Nutr, 50(3): 203-210.
Berggren, A.M., et al. (1993) "Short-chain fatty acid content and pH in caecum of rats given various sources of carbohydrates", J. Sci. Food. Agric., 63:397-406.
Bering, S., et al. (2006), "A lactic acid-fermented oat gruel increases non-haem iron absorption from a phytate-rich meal in healthy women of childbearing age", British Journal of Nutrition, 96(1): 80-85.
Bering, S., et al. (2007), "Viable, lyophilized lactobacilli do not increase iron absorption from a lactic acid-fermented meal in healthy young women, and no iron absorption occurs in the distal intestine", British Journal of Nutrition, (98)5: 991-997.
Bush, R., et al. (2013), "Randomized, Double Blind and Placebo Controlled Study Using a Combination of Two Probiotic Lactobacilli to Alleviate Symptoms and Frequency of Common Cold", Food and Nutrition Sciences, 4(11A): 13-20.
Cunningham-Rundles, S., et al. (2002), "Development of immunocompetence: Role of Micronutrients and Microorganisms", Nutrition Reviews, 60(5 Pt 2): S68-S72.
David L. Topping and Peter M. Clifton, "Short-Chain Fatty Acids and Human Colonic Function: Roles of Resistant Starch and nonstarch Polysaccharides," Physiological Reviews, 81(3):1031-1064, (2001).
Derwent, 2007, Derwent Abstract for RU 2284703, Accession No. 2007-069807, Abstract only cited, pp. 1-2.
Di Sabatino, A., et al., "Oral butyrate for mildy to moderately actve Crohn's disease," Alimentary Pharmacology & Therapeutics, 22(9):789-794, (2005).
Ducrotté, P., et al. (2012), "Clinical trial: Lactobacillus plantarum 299v (DSM 9843) improves symptoms of irritable bowel syndrome" World Journal of Gastroenterology, 18(30): 4012-4018.
Eccles, R. (2005), "Understanding the symptoms of the common cold and influenza", Lancet Infect Dis., 5(11): 718-725.
Eeckhaut, V., et al. (2009) "The anaerobic butyrate-producing strain butyricicoccus pillicaecorum decreases colonic inflammation and ulceration in TNBS-induced colitis rat model" 5th Probiotics Prebiotics New Foods, Sep. 13-15, Universita Urbania, Rome.
Fendrick, A., et al. (2003), "The Economic Burden of Non-Influenza-Related Viral Respiratory Tract Infection in the United States", Arch Intern Med., 163(4):487-494.
Gastrointestinal disorders [http://probi.se/sites/all/files/attachment_files/gastrointestinal_disorders.pdf].
Hoppe, M., et al. (2015), "Probiotic strain Lactobacillus plantarum 299v increases iron absorption from an iron-supplemented fruit drink: a double-isotope cross-over single-blind study in women of reproductive age", British Journal of Nutrition, 114(8): 1195-1202.
IBD News (2007) "Treatment of inflammatory bowel disease by probiotics", 36:1-2—Partial English Translation Only.
Immune system [http://probi.se/sites/all/files/attachment_files/immune_system_2015.pdf].
Increased iron absorption [http://probi.se/sites/all/fiies/attachment_files/iron_absorption_nov_2015.pdf].
International Preliminary Report on Patentability dated Mar. 19, 2012.
Johansson, M., et al. (1998), "Survival of Lactobacillus plantarum DSM 9843 (299v), and effect on the short-chain fatty acid content of faeces after ingestion of a rose-hip drink with fermented oats", International Journal of Food Microbiology, 42(1-2) 29-38.
Johansson, M.-L, et al. (1993) "Administration of different lactobacillus strains in fermented oatmeal soup: in vivo colonization of human intestinal mucosa and effect on the indigenous flora" Applied and Environmental Microbiology, vol. 59, No. 1, pp. 15-20.
Józefiak, D., et al. (2005) "The effect of supplementing a sumbiotic, organic acids, or b-glucanase to barley-based diets on the performance of broiler chickens", Journal of Animal and Feed Sciences, 14, Suppl. 1:447-450.
Kanauchi, O., et al. (2009) "The therapeutic impact of manipulating microbiota in inflammatory bowel disease" Current Pharmaceutical Design, vol. 15, pp. 2074-2086.
Karlsson, C., et al. (2010), "Probiotic therapy to men with incipient arteriossclerosis initiates increased bacterial diversity in colon: a randomized controlled trial", Atherosclerosis 208:228-233.
King, S., et al. (2014), "Effectiveness of probiotics on the duration of illness in healthy children and adults who develope common acute respiratory infectious conditions: a systematic review and meta-analysis", British Journal of Nutrition, 112(1): 41-54.
Kirkpatrick, G. (1996), "The Common Cold", Primary Care, 23(4): 657-675.
Klarin, B., et al. (2008), "Lactobacillus plantarum 299v reduces colonisation of Clostridium difficile in critically ill patients treated with antibiotics", Acta Anaesthesiol Scand, 52(8): 1096-1102.
Krag, A., et al. (2012), "Safety and efficacy of Profermin to induce remission in ulcerative colitis", World Journal of Gastroenterology, 18(15): 1773-1780.

(56) References Cited

OTHER PUBLICATIONS

Krag, A., et al. (2013), "Profermin is Efficacious in Patients with Active Ulcerative Colitis—A Ranidomized Controlled Trial", Inflamm Bowel Dis, 19(12): 2584-2592.

Lavansi, S., et al. (2010), "A Novel Probiotic Mixture Exerts a Therapeutic Effect on Experimental Autoimmune Encephalomyelitis Mediated by IL-10 Producing Regulatory T Cells", PLoS One, 5(2): e9009.

Lenoir-Wijnkoop, I., et al. (2015), "Public Health and Budget Impact of Probiotics on Common Respiratory Tract Infections: A Modelling Study", PLoS One, 10(4): e0122765.

Lomax, A., et al. (2009), "Probiotics, Immune Function, Infection and Inflammation: A Review of the Evidence from Studies Conducted in Humans", Current Pharmaceutical Design, 15(13): 1428-1518.

Lönnermark, E., et al. (2009), "intake of Lactobacillus plantarum Reduces Certain Gastrointestinal Symptoms During Treatment With Antibiotics", J Clin Gastroenterol, 00(00): 1-7.

Mack, D., et al. (1999), "Probiotics inhibit enteropathogenic *E. coli* adherence in vitro by inducing intestinal mucin gene expression", the American Physiological Society, 276 (4 Pt 1): G941-G950.

Mack, D., et al. (2003), "Extracellular MUC3 mucin secretion follows adherence of Lactobacillus strains to intestinal epithelial cells in vitro", Gut, 52(6): 827-833.

McCracken, V., et al. (2002), "TNF-alpha Sensitizes HT-29 Colonic Epithelial Cells to Intestinal Lactobacilli", Exp Biol Med, 227(8):665-670.

McNaught, C., et al. (2005), "A prospective randomised trial of probiotics in critically ill patients", Clinical Nutrition, 24(2): 211-219.

Metabolic syndrome [http://probi.se/sites/aii/files/attachment_files/metabolic_syndrome.pdf].

Molin (2015) Lactobacillus paracasei 8700:2. Oct. 29, 2015. [http://probi.se/sites/all/files/attachment_files/l-paracasei-8700-kolon2-15_2015-10-29_0.pdf].

Molin (2015) Lactobacillus plantarum 299. Jun. 10, 2015. [http://probi.se/sites/all/files/attachment_files/lp_299-15.2015-06-10_0.pdf].

Molin (2015) Lactobacillus plantarum 299v. Oct. 29, 2015. [http://probi.se/sites/all/files/attachment_files/lp_299v-15_2015-10-29_0.pdf].

Molin (2015) Lactobacillus plantarum HEAL19. Oct. 29, 2015. [http://probi.se/sites/all/fiies/attachment_files/heal19-15_2015-10-29_0.pdf].

Molin (2015) Lactobacillus plantarum HEAL9. Oct. 29, 2015. [http://probi.se/sites/all/files/attachment_files/heal9-15_2015-10-29_0.pdf].

Molin (2015) Lactobacillus rhamnosus 271. Nov. 4, 2015. [http://probi.se/sites/all/files/attachment_files/l_ramnosus_271_2015_0.pdf].

Mussatto et al., 2006, Journal of Cereal Science, 43, 1-14.

NON-FERMENTED COMPOSITIONS COMPRISING A CEREAL BASED FRACTION AND A PROBIOTIC AND USES THEREOF

PRIORITY STATEMENT

This application is a divisional of U.S. Ser. No. 13/513,290 filed on 1 Jun. 2012, which is a national phase application under 35 U.S.C. § 371 of PCT International Application No. PCT/SE2010/051464 which has an International filing date of 22 Dec. 2010, which claims priority under 35 U.S.C. § 119 to Swedish Patent Application No. 0951011-6, filed on 22 Dec. 2009. The contents of each application recited above are incorporated herein by reference in their entirety.

TECHNICAL FIELD OF THE INVENTION

The present invention relates to a non-fermented composition having the ability to increase the formation of butyric acid in the colon, as well as to different uses of said non-fermented composition such as for the maintenance of a healthy gut-mucosa by the provision of an increased barrier function.

BACKGROUND ART

Butyric acid and glutamine have been proposed to be important for colonic health. Pure barley β-glucans have been shown to give comparatively high amounts of butyric acid, and germinated barley foodstuff, obtained from brewer's spent grain (BSG), containing high amounts of β-glucans and glutamine, has been reported to reduce the inflammatory response in the colon of subjects with ulcerative colitis.

There has been much recent interest in the relationship between dietary fiber, health-promoting bacteria and the prevention of inflammatory bowel diseases, which include Crohn's disease and ulcerative colitis.

Dietary fiber is resistant to digestion in the small intestine and is therefore available for fermentation by the microbial flora in the large intestine, forming short-chain fatty acids (SCFA) together with gases and heat. The principal SCFA formed are acetic, propionic and butyric acids, while valeric, caproic, heptanoic acids and the branched iso-butyric and iso-valeric acids are formed in lesser amounts. The SCFA are absorbed and transported via the portal vein to the liver, and the fraction not absorbed is excreted in feces. Propionic acid is a substrate for hepatic gluconeogenesis and has been reported to inhibit cholesterol synthesis, while acetic acid has been shown to stimulate the gluconeogenesis and the formation of cholesterol via acetyl-CoA. Butyric acid is the major energy source for colonocytes, and has been hypothesized to reduce the risk of colon cancer and to benefit IBD. Recently, butyric acid has also been suggested to have metabolic effects.

Besides dietary fiber, small amounts of protein will also reach the colon. In this sense glutamine is one amino acid of special interest. Glutamine, together with butyric acid, is an important substrate for the colon epithelial cells. This is of interest since the presence of high amounts of butyric acid in colon will reduce the epithelial cells' need for glutamine, and in this way increase the glutamine levels in the blood. High levels of glutamine in the circulating system have been found to be positive since it improves the immune defense.

Cereal-based foods have been used for a very long time, and the cereal grains contain the protein, fat and carbohydrate required by humans for growth and maintenance. Fermentation of barley may produce high amounts of butyric acid, due to its high content of β-glucans, and it has been shown that germinated barley foodstuff (GBF) contains high amounts of glutamine. Glutamine in GBF has been reported to be bound to the dietary fiber and reach the large intestine, where it can be liberated during fermentation and be a substrate for the colonic mucosa. In studies where GBF has been used, the symptoms and inflammations were ameliorated in rats induced with dextran sulfate sodium (DSS) colitis. The same effect was seen in humans with ulcerative colitis.

Probiotic bacteria are defined as live microorganisms which when administered in adequate amounts beneficially affect the host. Lactobacilli and bifidobacteria are the most frequently used bacteria in probiotic products. These bacteria are generally safe, as are probiotics based on these organisms. The lack of pathogenicity extends across all age groups and to immunocompromised individuals. Intake of different probiotic bacteria has been shown to have clinical benefits in various physiologic or pathologic situations. The most clear cut effects have been shown in diarrhea caused by antibiotic therapy or rotavirus infection. There are also studies showing positive clinical effects in inflammatory bowel diseases, atopic dermatitis and hypercholesterolemia after intake of probiotic bacteria. The mechanism, by which probiotic bacteria contribute to these clinical improvements are not clear. *Lactobacillus rhamnosus* is one of the largest bacterial groups represented in the bowel of healthy individuals. High amounts of probiotic bacteria may obstruct the proliferation of pathogenic bacteria. A combination of pre- and probiotics may not only affect the microbiota but also optimize the formation of CA.

WO2007036230 discloses a ready-to-use product comprising fermented cereal and non-pathogenic microorganisms, wherein the fermented cereal is preferably oatmeal. The present invention differs from WO2007036230 by the fact that the present compositions are non-fermented and There is a need for novel approaches of how to keep the gut-mucosa healthy by providing an increased barrier function of the gut.

The aim of the present invention is to investigate the potential role of a few cereal based fractions, such as different barley fractions, as a prebiotic product, regarding the cecal formation of CA, levels of SCFA and amino acids in blood, and the cecal composition of the bacterial flora (lactobacilli, bifidobacteria, Enterobacteriacece), and whether the addition of a probiotic strain would give any further effects.

SUMMARY OF THE INVENTION

Thus, the present invention relates, in one aspect, to a non-fermented composition having the ability to increase the formation of butyric acid in the colon and comprising at least one cereal based fraction and at least one isolated probiotic strain of *Lactobacillus*.

The present invention relates, in a further aspect, to the use of said non-fermented composition as a synbiotic.

The present invention relates, in a yet further aspect, to said non-fermented composition, for use in treatment of the metabolic syndrome, ulcerative colitis, Crohns disease, Irritable bowel syndrome (IBS), or Inflammatory bowel disease (IBD).

The present invention relates, in a yet further aspect, to said non-fermented composition, for use in the maintainance of a healthy gut-mucosa and/or for the provision of an increased barrier function of the gut-mucosa.

DETAILED DESCRIPTION OF EMBODIMENTS OF THE INVENTION

The present invention relates to a non-fermented composition having the ability to increase the formation of butyric acid in the colon and comprising at least one cereal based fraction and at least one isolated probiotic strain of *Lactobacillus*. The meaning of the phrase "having the ability to increase the formation of butyric acid in the colon" means that the present non-fermented composition comprising both a probiotic and a cereal based fraction will increase the formation of butyric acid in the colon and in blood, see table 4 and 5, compared to when a cereal based fraction is given only without a probiotic. In table 4 the formation of butyric acid in the colon has increased 157% (from 7 to 18 μmol/g) for whole grain barley, 50% (from 12 to 18 μmol/g) for malted barley and 33% (from 9 to 12 μmol/g) for Brewers spent grain. Thus, an increase of the formation of butyric acid is in the range of 30-200%, preferably in the range of 40-180%, more preferably in the range of 50-160%. Alternatively, put in other words, the butyric acid content formed in the colon is in the range of 14-20 μmol/g or >14 μmol/g.

In the present context the phrase "non-fermented composition" should be interpreted as the not yet consumed composition. It is intended that the fermentation should occur in the gastrointestinal tract after consuming the composition. The organic acids formed during gastrointestinal fermentation are measured in blood and cecal contents. In dried products of the invention such as cereals, muesli, breads, biscuits, cereals, health bars, or spreads the organic acids are not present in the composition due to non-fermentation. In the wet products the bacteria could be present in an encapsulated form preventing them from fermenting the composition before entering the gastrointestinal tract. Another approach for preventing fermentation is keeping the composition at a low temperature, i.e. keeping the composition refrigerated or frozen at appropriate temperatures and shelf life. The non-fermented compositions of the invention may be a dried composition and fluid composition.

In table 5 the butyric acid content formed in portal blood has been measured. The increase for WGB is 133% (46 to 107 μmol/L), for malted barley 117% (from 96 to 208 μmol/L), and for BSG 56% (53 to 83 μmol/L). Thus, for all three barley fractions the butyric acid content is >80 μmol/L.

The cereal based fraction is present in the non-fermented composition in the range of 40-100% weight. The remaining contents of the composition are apparent to a person skilled in the art of formulating synbiotic compositions.

The results of the present invention are very unexpected and the increase of the butyric acid formation that has been observed has been doubled when giving a composition according to the invention compared to when giving the cereal based fraction only, see table 4 and 5.

In one embodiment of the invention the at least one cereal based fraction of the composition is a whole grain cereal fraction such as a whole grain barley, a whole grain oat, a whole grain wheat, a whole grain rye or a combination thereof. The at least one cereal based fraction used in the composition of the invention may have been processed in different ways before being added to the present composition, for instance the cereal based fraction could be a milled and/or heat treated cereal based fraction, or an extruded, expanded cereal based fraction, or a drum-dried cereal based fraction, or a flaked cereal based fraction or a steam-cooked cereal based fraction.

In a further embodiment of the invention the at least one cereal based fraction is chosen from the group of a barley fraction, an oat fraction, a wheat fraction, a rye fraction and any combination thereof. The at least one cereal based fraction may additionally be malted and in one embodiment of the invention the malted cereal based fraction is malt or brewer's spent grain (BSG), which is a by-product of the brewing process. In the first step, when brewing beer, barley is germinated and then roasted. The malt is crushed and mixed with water and the mixture is heated. BSG is the by-product when the mixture is filtrated and the filtrate continues to the next brewing processing step. BSG has often been used as cattle feed, but results from earlier studies indicate that it is of interest to examine whether BSG may be used as prebiotics in human food.

In an embodiment of the invention the cereal based fraction has been milled in order to have a suitable size in the composition, wherein the size of the at least one cereal based fraction is in the range of approximately 0.1 mm-10 mm, preferably 0.5 mm to 5 mm.

The at least one isolated strain of *Lactobacillus* is present in an amount of $10^6$-$10^{14}$ CFU/day, preferably $10^8$-$10^{12}$ CFU/day, more preferably $10^9$-$10^{11}$ CFU/day. CFU stands for colony forming units and is a well known unit for a person skilled in the art of probiotics.

In an embodiment of the invention the at least one isolated probiotic strain is chosen from the group of *Lactobacillus plantarum, Lactobacillus paraplantarum, Lactobacillus pentosus, Lactobacillus rhamnosus, Lactobacillus paracasei* and *Lactobacillus fermentum*.

In one embodiment of the invention the at least one isolated probiotic strain is a *Lactobacillus rhamnosus* 271 (DSM 6594). In another embodiment the at least one probiotic strain is chosen from the group of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

*Lactobacillus plantarum* 299, DSM 6595, and *Lactobacillus rhamnosus* 271 (DSM 6594) were deposited on 2 Jul. 1991 at the Deutsche Sammlung von Mikroorganismen und Zellkulturen GmbH, *Lactobacillus plantarum* 299v, DSM 9843, was deposited on 16 Mar. 1995 at the Deutsche Sammlung von Mikroorganismen und Zellkulturen GmbH, *Lactobacillus plantarum* HEAL 9, DSM 15312, *l Lactobacillus plantarum* HEAL 19, DSM 15313, and *Lactobacillus plantarum* HEAL 99, DSM 15316, were deposited on Nov. 27, 2002, at the Deutsche Sammlung von Mikroorganismen und Zellkulturen GmbH. The at least one probiotic may be present in the composition as a freeze-dried component, in the form of a probiotic in an oil, in the form of a probiotic in a aqueous solution or suspension, in the form of spray-dried probiotic, or in the form of probiotic in a hard fat state.

In an embodiment of the invention said composition is a liquid formulation or a solid formulation. When preparing the compositions of the invention, either in a liquid or a solid state, conventional additives as used in the technical field will be used and are realized by a person skilled in the technical field.

In another embodiment said composition is a medical food, a functional food, a dietary supplement, a nutritional product, a food or a food additive. The food additive could for instance be added to cereals, muesli, breads, biscuits, cereals, health bars, or spreads as a mixed powder composition or each component separately. An example of the latter is for instance the spreading of the cereal based fraction onto the relevant food such as muesli and thereafter adding the relevant probiotic strain. The beneficial effects of the invention are obtained when the cereal based fraction and the probiotic strains are taken together. It should be understood that it is not necessary the combination is given as a composition. It is for instance possible to mix the components precisely before intake.

In another embodiment of the invention the food is a drink, a beverage, a yoghurt, a juice or an ice cream. Thus, it is realized that the composition could be easily taken in the form of a food on a daily basis. Thus, the general health of mankind could become better by the use of the composition according to the invention.

The composition of the present invention may be used as a synbiotic. A synbiotic is a supplement that contains both a prebiotic and a probiotic that work together to improve the "friendly flora" of the human intestine.

In a further embodiment the invention relates to the use of a composition, for treatment of the metabolic syndrome, ulcerative colitis, Crohns disease, Irritable bowel syndrome (IBS), or Inflammatory bowel disease (IBD).

In a yet another embodiment, the invention relates to a composition as defined herein for use in the maintenance of a healthy gut-mucosa and/or in the provision of an increased barrier function of the gut-mucosa.

EXPERIMENTAL

Material and Methods

Composition of Test Materials

The raw material used was whole grain barley (Viking Malt AB, Halmstad, Sweden), malt and brewer's spent grain (Carlsberg, Falkenberg, Sweden). Whole grain barley, malt and brewer's spent grain came from the same batch of flour. The raw materials were milled before being included in the diets to a paricle size in the range of about 1 mm. The bacterial strain included in the experiment was *L. rhamnosus* 271 (Probi AB, Lund Sweden) and it was delivered freeze-dried.

Animals and Experiment Design

Six test diets were prepared according to Table 1: one reference diet containing whole grain barley (WGB), and 5 test diets including whole grain barley and *L. rhamnosus* 271 (WGB+Lr), malt (Malt), malt and *L. rhamnosus* 271 (Malt+FLr), brewer's spent grain (BSG) or brewer's spent grain and *L. rhamnosus* 271 (BSG+Lr). The raw materials were added at a level of 80 g dietary fiber/kg diet (dwb, dry weight basis). Wheat starch was used to adjust the dry matter content, and this type of starch has previously been shown to be completely digested, and therefore does not form any CA. The probiotic strain was included daily in the diet at feeding time for each rat in the amount of $2 \times 10^8$ colony forming units (CFU)/d.

Table 1 shows the composition of the test diets given to rats in the following groups: whole grain barley (WGB), malt (Malt) or brewer's spent grain (BSG) with or without the addition of *L. rhamnosus* (Lr) (Table 1).

TABLE 1

| Diet ingredient[1] | WGB | WGB + Lr | Malt | Malt + Lr | BSG | BSG + Lr |
|---|---|---|---|---|---|---|
| Whole grain barley,[2] g | 519.5[3] | 519.5[3] | 0 | 0 | 0 | 0 |
| Malt,[4] g | 0 | 0 | 661.2[3] | 661.2[3] | 0 | 0 |
| Brew. spent grain,[4] g | 0 | 0 | 0 | 0 | 135.8[3] | 135.8[3] |
| Casein, g | 120 | 120 | 120 | 120 | 120 | 120 |
| DL-Methionine, g | 1.2 | 1.2 | 1.2 | 1.2 | 1.2 | 1.2 |
| Corn oil, g | 50 | 50 | 50 | 50 | 50 | 50 |
| Mineral mixture,[5] g | 48 | 48 | 48 | 48 | 48 | 48 |
| Vitamin mixture,[6] g | 8 | 8 | 8 | 8 | 8 | 8 |
| Choline chloride, g | 2 | 2 | 2 | 2 | 2 | 2 |
| Sucrose, g | 100 | 100 | 100 | 100 | 100 | 100 |
| Wheat starch,[7] g | 151.3 | 151.3 | 9.6 | 9.6 | 535.0 | 535.0 |

[1]Diet ingredients total 1000 g.

[2]Viking Malt AB (Halmstad, Sweden).

[3]Corresponding to 80 g dietary fiber/kg diet (dwb).

[4]Carlsberg (Falkenberg, Sweden).

[5]Containing (g/kg): 0.37CuSO$_4$•5H$_2$O, 1.4ZnSO$_4$•7H$_2$O, 332.1KH$_2$PO$_4$, 171.8NaH$_2$PO$_4$•2H$_2$O, 324.4CaCO$_3$, 0.068KI, 57.2MgSO$_4$, 7.7FeSO$_4$•7H$_2$O, 3.4MnSO$_4$•H$_2$O, 0.02CoCl•6H$_2$O, 101.7NaCl (Bie & Berntsen A-S, Rødovre, Denmark).

[6]Containing (g/kg): 0.62 menadione, 2.5 thiamin hydrochloride, 2.5 riboflavin, 1.25 pyridoxine hydrochloride, 6.25 calcium pantothenate, 6.25 nicotinic acid, 0.25 folic acid, 12.5 inositol, 1.25 p-aminobenzoic acid, 0.05 biotin, 0.00375 cyanocobalamin, 0.187 retinol palmitate, 0.00613 calciferol, 25 d-α-tocopheryl acetate, 941.25 maize starch (Apoteket, Malmö, Sweden).

[7]Wheat starch (Cerestar, Krefeld, Germany).

Male Wistar rats (initial weight, 134±1 g) were obtained from Scanbur (Sollentuna, Sweden). They were randomly divided into six groups, seven rats in each, and housed individually in metabolic cages, in a room maintained at 22° C., with 12-hour light/dark cycles. The feed intake was restricted to 12 g/d (dwb) and the rats were given free access to water. The animals were allowed to adapt to the diet for 7 d and then followed a 5-d long experimental period when feces and feed residues were collected daily. The fecal samples were stored at −20° C. and then freeze-dried and milled before analysis of dietary fiber. At the end of the experiment the animals were anaesthetized by subcutaneous injection of a mixture (1:1:2) of Hypnorm (Division of Janssen-Cilag Ltd., Janssen Pharmaceutica, Beerse, Belgium), Dormicum (F. Hoffman-La Roche AG, Basel, Switzerland) and sterile water at a dose of 0.15 ml/100 g and blood, cecal tissue and content were collected. The blood samples were drawn from the portal vein and sampled into two tubes: one for plasma containing EDTA and one for serum. The plasma and serum samples were centrifuged for 15 min (2500×g) and then stored at −40° C. until analysis of amino acids and SCFA. Cecal tissue weight, content and pH were measured directly. The cecal content was divided into one sterile tube containing freezing media and immediately frozen in liquid nitrogen for analysis of the microbiota and the other part of the cecal content was frozen and stored at −40° C. until analysis of the CA, which was also done for the different parts of the hindgut.

Analyses

Dietary fiber. A gravimetrical method was used to determine the amount of soluble and insoluble dietary fiber in the raw materials. The composition of the isolated fiber residue was analyzed using gas-liquid chromatography (GLC) of the neutral sugars as their alditol acetates, and the content of uronic acids was analyzed with a spectrophotometric method. The fiber monomers in feces were characterized directly without prior isolation of dietary fiber.

CA in feces. A GLC method was used to analyze the SCFA (acetic, propionic, isobutyric, butyric, isovaleric, valeric, caproic, and heptanoic acids) in the intestinal content (cecum, proximal and distal colon). Dilution solution (2.5 M HCl) and 2-ethylbutyric acid (internal standard, 1 mM) were added to the samples before homogenization. The samples were then centrifuged before injection onto a fused-silica capillary column.

Succinic and lactic acid were quantified spectrophotometrically with commercially available enzymatic kits (Cat. Nos. 10176281035 and 1112821, respectively; Boehringer Mannheim, Mannheim, Germany). The procedures were performed according to the manufacturer's instructions.

SCFA in serum. The SCFA in serum were analyzed with a GLC method. Water and 2-ethylbutyric acid (internal standard, 1 mM) together with hydrochloric acid were added to the samples, and then a hollow fiber was immersed in the serum solution to extract the SCFA. After extraction, the SCFA were flushed from the fiber lumen and then injected onto a fused-silica capillary column (DB-FFAP 125-3237, J&W Scientific, Agilent Technologies Inc., Folsom, Calif. U.S.A.). GC ChemStation software (Agilent Technologies Inc., Wilmington, Del., U.S.A.) was used for the analysis.

Amino acid content in plasma. Sulfosalicylic acid was added to the plasma samples to purify free amino acids by precipitating high-molecular-weight proteins. An amino acid analyzer (Biochrom 30, Biochrom Ltd, Cambridge, England) based on ion-exchange chromatography was used to quantify the amount of amino acids. The EZChrom Elite software package (Scientific Software Inc., Pleasanton, Calif., U.S.A.) was used for the analysis.

Intestinal microbiota. The cecal samples were thawed and after homogenization a conventional serial dilution procedure was completed and appropriate dilutions were spread onto agar plates. Viable counts were obtained from Rogosa agar (Oxoid, Unipath Ltd., Basingstoke, UK) incubated anaerobically at 37° C. for 72 h (Lactobacilli counts), from Modified Wilkins-Chalgren agar (Oxoid) incubated anaerobically at 37° C. for 72 h (bifidobacteria counts), and from violet red-bile glucose agar VRBG (Oxoid) incubated aerobically at 37° C. for 24 h (Enterobacteriaceae counts). The number of colonies formed on each plate was counted and corrected for the weight of the original samples.

Calculations and Statistical Analyses

The concentration of each CA (µmol/g) was multiplied by the amount of cecal content to obtain the cecal pools (µmol). To correct for the small amounts of feed residues the pool values were extrapolated to the complete intake of dietary fiber (4.8 g). Body weight gain during the experimental period was calculated per gram feed consumed.

To determine the effects of dietary fiber (Fiber), probiotics (Pro) and their interactions (Fiber×Pro) 2-way ANOVA was used (Table 3-5 and 7). One-way ANOVA was used for individual means to assess the effect of dietary fiber or the probiotic effect by using Tukey's procedure. When error variance was found to be heterogeneous, data were transformed by BoxCox-transformation before ANOVA. Values are presented as means±SEM and differences resulting in P values less than 0.05 were considered significant. All evaluations were performed with Minitab statistical software (Release 14).

Results

Fecal Excretion of Dietary Fiber

The dietary fiber content was similar in whole grain barley and malt (15.4 and 12.1 g/100 g, dwb, respectively), while brewer's spent grain contained 4-5 times more dietary fiber (58.2 g/100 g, dwb). The main components of the dietary fiber polysaccharides were glucose (35-49%), xylose (29-35%) and arabinose (16-22%). Dietary fiber polysaccharides in whole grain barley and brewer's spent grain were more fermented in the rat colon than malt (Table 2). Fifty-six percent of the fiber in malt was excreted in feces, while 38% and 49%, respectively of the fiber in whole grain barley and brewer's spent grain was excreted (P<0.001). Of the main components xylose was similarly fermented 45±4%, while arabinose and above all glucose were fermented to different degrees (P<0.01 and P<0.001, respectively). Glucose-containing polymers were most resistant to fermentation in malt (72% was excreted in feces) and most fermented in whole grain barley (36% was excreted in feces). No differences in the degree of fermentation could be seen when Lr was added to the diets, an exception being the small amounts of uronic acids present, that was more fermented with Lr in the diet than whole grain barley only (P=0.040).

TABLE 2

|  | WGB g/100 g | WGB % of intake | WGB + Lr % of intake | Malt g/100 g | Malt % of intake | Malt + Lr % of intake | BSG g/100 g | BSG % of intake | BSG + Lr % of intake |
|---|---|---|---|---|---|---|---|---|---|
| Rhamnose | tr[1] | tr[1] | tr[1] | tr[1] | tr[1] | tr[1] | tr[1] | tr[1] | tr[1] |
| Arabinose | 2.0 | 33[a] | 35 | 1.7 | 40[b] | 37 | 7.7 | 36[a,b] | 36 |
| Xylose | 3.5 | 43 | 41 | 2.7 | 49 | 48 | 12.1 | 45 | 45 |
| Mannose | 0.3 | 19[a] | 18 | 0.2 | 34[b] | 33 | 0.5 | 37[b] | 40 |
| Galactose | 0.2 | 66[a] | 72 | 0.2 | 68[a] | 67 | 1.1 | 51[b] | 54 |
| Glucose | 5.9 | 36[a] | 35 | 2.7 | 72[b] | 68 | 13.8 | 57[c] | 58 |
| Uronic acid | 0.3 | 64 | 56* | 0.3 | 56 | 55 | 1.3 | 59 | 60 |
| Dietary fiber polysaccharides | 12.2 | 38[a] | 38 | 7.8 | 56[b] | 54 | 36.7 | 49[c] | 49 |
| Lignin | 3.2 | nd[2] | nd[2] | 4.3 | nd[2] | nd[2] | 21.5 | nd[2] | nd[2] |
| Total | 15.4 | nd[2] | nd[2] | 12.1 | nd[2] | nd[2] | 58.2 | nd[2] | nd[2] |

[1]tr = traces, less than 0.05 g/100 g.

[2]nd = not determined.

Feed Intake and Body Weight Gain

Rats in the different groups ate most of the diet provided (56.6-59.3 g/5 d). Further, the body weight gain, and cecal content, tissue weight and pH were quite similar between these groups (Table 3). When probiotics were added to the diets some differences could be seen. There was a higher body weight gain in rats with BSG (P=0.044), and a higher cecal content and tissue weight together with WGB (P=0.019 and P=0.004, respectively). A lower cecal pH could be seen with WGB (P=0.011) and with Malt (P=0.032). The bulking capacity was higher in rats fed Malt compared with the other products (P<0.001).

The Formation of CA in the Hindgut of Rats

Rats fed Malt had a higher level and pool of CA than rats fed WGB (79 versus 62 μmol/g, P=0.027 and 173 versus 116 μmol, P=0.037, respectively), while the two other barley fractions had similar cecal levels (62-66 μmol/g) and pools (123-173 μmol) of CA (Table 4). In general, the probiotic strain affected the cecal levels of more individual CA than the different fiber fractions. However, individual significant differences between diets containing *L. rhamnosus* and their corresponding diets without this probiotic strain were only seen in rats fed WGB. The major acid formed in cecum of rats fed the six test diets was acetic acid (62±3%), followed by butyric acid (15±4%) and propionic acid (14±1%).

TABLE 3

|  | WGB | WGB + Lr | Malt | Malt + Lr | BSG | BSG + Lr | P-value Fiber | P-value Pro | P-value Fiber × Pro |
|---|---|---|---|---|---|---|---|---|---|
| BWG | 0.21 | 0.25 | 0.17 | 0.21 | 0.18 | 0.25* | NS | 0.006 | NS |
| CC | 1.8 ± 0.1 | 2.3 ± 0.1* | 2.2 ± 0.1 | 2.2 ± 0.1 | 1.8 ± 0.1 | 1.7 ± 0.1 | 0.002 | NS | NS |
| CTW | 0.56 ± 0.01 | 0.63 ± 0.01** | 0.57 ± 0.02 | 0.58 ± 0.03 | 0.53 ± 0.02 | 0.54 ± 0.02 | 0.011 | NS | NS |
| Cecal pH | 7.1 | 6.7* | 7.0 | 6.8* | 7.1 | 7.0 | NS | 0.001 | NS |
| BC | 0.8 ± 0.0[a] | 0.8 ± 0.0 | 1.0 ± 0.0[b] | 0.9 ± 0.0* | 0.8 ± 0.0[a] | 0.8 ± 0.0 | <0.001 | NS | NS |

BWG means body weigh gain g/g

CC means cekal content, g

CTW means cekal tissue weight, g

BC means bulking capacity, g/g fiber ingested

[1]Values are means ± SEM, n = 7. Malt + Lr, n = 6

[2]Mean values of WGB, Malt and BSG, i.e. those without any added probiotics, with dissimilar superscript letters were significantly different (P < 0.05).

[3]Mean values were significantly different from those for rats fed diets without bacteria:

*P < 0.05,

**P < 0.01.

TABLE 4

|  | WGB | WGB + Lr | Malt | Malt + Lr | BSG | BSG + Lr | Fiber | Pro | Fiber × Pro |
|---|---|---|---|---|---|---|---|---|---|
| Cecal level | | | | | | | | | |
| Acetic | 39 ± 1$^a$ | 55 ± 7* | 49 ± 3$^b$ | 61 ± 6 | 41 ± 4$^{a,b}$ | 51 ± 3 | NS | 0.001 | NS |
| Propionic | 9 ± 1 | 13 ± 1* | 11 ± 0 | 13 ± 1 | 9 ± 1 | 11 ± 1 | 0.021 | <0.001 | NS |
| Butyric | 7 ± 0$^a$ | 18 ± 5* | 12 ± 1$^b$ | 18 ± 3 | 9 ± 1$^{a,b}$ | 12 ± 2 | NS | 0.001 | NS |
| Lactic | 0.1 ± 0.0$^a$ | 0.2 ± 0.1 | 0.3 ± 0.1$^b$ | 0.2 ± 0.0 | 0.4 ± 0.1$^b$ | 0.4 ± 0.1 | 0.013 | NS | NS |
| Succinic | 2 ± 0 | 2 ± 0 | 2 ± 0 | 1 ± 0 | 2 ± 0 | 1 ± 0 | NS | NS | NS |
| Minor | 4 ± 0 | 6 ± 1* | 5 ± 0 | 5 ± 0 | 5 ± 0 | 5 ± 0 | NS | 0.010 | 0.026 |
| Total | 62 ± 2$^a$ | 94 ± 13* | 79 ± 4$^b$ | 99 ± 10 | 66 ± 6$^{a,b}$ | 80 ± 5 | NS | 0.001 | NS |
| Total pool | 116 ± 11$^a$ | 228 ± 41* | 173 ± 10$^b$ | 225 ± 34 | 123 ± 20$^{a,b}$ | 141 ± 6 | 0.009 | 0.002 | NS |
| Distal level | | | | | | | | | |
| Acetic | 37 ± 1 | 39 ± 3 | 38 ± 2 | 46 ± 2* | 37 ± 5 | 29 ± 2 | 0.004 | NS | 0.013 |
| Propionic | 8 ± 0 | 10 ± 1* | 10 ± 1 | 13 ± 1* | 8 ± 1 | 7 ± 0 | <0.001 | NS | 0.015 |
| Butyric | 6 ± 0$^a$ | 8 ± 1 | 9 ± 1$^b$ | 10 ± 1 | 6 ± 1$^{a,b}$ | 6 ± 0 | <0.001 | NS | NS |
| Minor | 4 ± 0 | 4 ± 0 | 4 ± 0 | 4 ± 0 | 4 ± 0 | 3 ± 0 | 0.044 | NS | NS |
| Total | 55 ± 1 | 61 ± 4 | 62 ± 3 | 73 ± 4* | 55 ± 6 | 44 ± 3 | <0.001 | NS | 0.016 |

[1]Values are means ± SEM, n = 7. Malt + Lr, n = 6. Distal: Malt + Lr, n = 6; WGB, BSG, n = 5.
[2]Mean values of WGB, Malt and BSG, i.e. those without any added probiotics, with dissimilar superscript letters were significantly different (P < 0.05).
[3]Mean values were significantly different from those for rats fed diets without bacteria:
*P < 0.05,
**P < 0.01.
The cekal level is given in μmol/g.

The cecal level of acetic acid in rats fed Malt was higher than in rats fed WGB (P=0.035), which could also be seen with butyric (P=0.016) and lactic acid (P=0.024). Further, rats given BSG had a higher level of lactic acid than the WGB group (P=0.003). The levels of all acids, except for lactic and succinic acid levels, were higher when probiotics were added to the WGB group (P=0.011-0.033).

The levels in the proximal and distal part of colon (data not shown) were very similar to the different test diets (46-56 μmol/g and 44-73 μmol/g, respectively). In the distal part of the colon, the fiber fraction generally had a greater impact on the CA levels than L. rhamnosus. However, there was only one individual difference between test materials concerning butyric acid levels, i.e. rats fed WGB had a lower level of butyric acid than rats fed Malt (P=0.025). The levels of acetic and propionic acid and the total distal level were higher in rats fed Malt supplemented with L. rhamnosus compared with Malt only (P=0.02, P=0.048 and P=0.038, respectively). A higher propionic acid level was also found in rats given WGB+Lr than in rats fed WGB only (P=0.047).

Level of SCFA in Portal Blood

Acetic acid (976-1596 μmol/l), propionic acid (72-195 μmol/l) and butyric acid (46-208 μmol/l) were the major acids in the portal blood (Table 5). Rats fed Malt had higher levels of propionic acid and butyric acid in portal blood than rats given WGB (P=0.039 and P=0.011, respectively) and BSG (P=0.020 and P=0.032, respectively). Rats given Malt+Lr had a very high butyric acid level in portal blood, compared with the Malt group. The difference in butyric acid level was not significant, but very close to it (P=0.055). The minor acids (iso-butyric, iso-valeric and valeric acids) were higher in the portal blood of rats fed WGB+Lr than those rats fed only WGB (P=0.040).

TABLE 5

|  | WGB | WGB + Lr | Malt μmol/L | Ma + Lr | BSG | BSG + Lr | Fiber | Pro | Fiber × Pro |
|---|---|---|---|---|---|---|---|---|---|
| Acetic | 1193 ± 95 | 1223 ± 156 | 1175 ± 94 | 1596 ± 307 | 976 ± 35 | 1185 ± 215 | NS | NS | NS |
| Propionic | 77 ± 10$^a$ | 131 ± 24 | 131 ± 18$^b$ | 195 ± 56 | 72 ± 7$^a$ | 102 ± 23 | 0.028 | 0.043 | NS |
| Butyric | 46 ± 5$^a$ | 107 ± 27 | 96 ± 14$^b$ | 208 ± 84 | 53 ± 7$^a$ | 83 ± 22 | 0.023 | 0.009 | NS |
| i-Butyric | 15 ± 1$^{a,b}$ | 22 ± 3 | 21 ± 3$^b$ | 32 ± 5 | 13 ± 1$^a$ | 17 ± 2 | 0.003 | 0.006 | NS |
| i-Valeric | 16 ± 1 | 25 ± 3* | 21 ± 2 | 25 ± 3 | 16 ± 3 | 19 ± 2 | NS | 0.016 | NS |
| Valeric | 6 ± 1$^{a,b}$ | 13 ± 3 | 11 ± 2$^b$ | 16 ± 4 | 5 ± 1$^a$ | 8 ± 2 | NS | 0.026 | NS |
| Minor | 37 ± 2 | 60 ± 9* | 53 ± 6 | 73 ± 7 | 35 ± 5 | 45 ± 6 | 0.004 | 0.002 | NS |
| Total | 1354 ± 100 | 1520 ± 186 | 1454 ± 130 | 2071 ± 451 | 1136 ± 45 | 1414 ± 263 | NS | NS | NS |

[1]Values are means ± SEM, Malt, n = 6; WGB, WGB + Lr, Malt + Lr, BSG, n = 5; BSG + Lr, n = 4.
[2]Mean values of WGB, Malt and BSG, i.e. those without any added probiotics, with dissimilar superscript letters were significantly different (P < 0.05).
[3]Mean values were significantly different from those for rats fed diets without bacteria:
*P < 0.05.

Composition of Amino Acids in Barley Products

The total amounts of amino acids were approximately the same in whole grain barley and malt (9.7 g/100 g and 9.5 g/100 g), whereas brewer's spent grain contained considerably more (24.3 g/100 g) (Table 6). The amino acid pattern of the barley products was similar to the highest proportion of glutamic acid, followed by proline, leucine and asparagine acid.

TABLE 6

|  | Whole grain barely | Malt | Brew. spent grain |
|---|---|---|---|
| Asparagine acid, % | 6 | 7 | 7 |
| Threonine, % | 3 | 4 | 4 |
| Serine, % | 5 | 4 | 4 |
| Glutamic acid, % | 23 | 20 | 20 |
| Proline, % | 12 | 11 | 10 |
| Glysine, % | 4 | 4 | 4 |
| Alanine, % | 4 | 5 | 5 |
| Valine, % | 5 | 6 | 6 |
| Cysteine, % | 3 | 3 | 2 |
| Methionine, % | 2 | 2 | 2 |
| Iso-leucine, % | 4 | 4 | 4 |
| Leucine, % | 7 | 7 | 8 |
| Tyrosine, % | 3 | 3 | 4 |
| Phenylalanine, % | 5 | 5 | 6 |
| Lysine, % | 4 | 4 | 4 |
| Histidine, % | 2 | 3 | 2 |
| Arginine, % | 5 | 5 | 5 |
| $NH_4$, % | 3 | 3 | 2 |
| Total, g/100 g | 9.7 | 9.5 | 24.3 |
| Total intake, g/5 d | 3.0 | 3.8 | 2.0 |

Distribution of Amino Acids in Portal Blood

There were detectable amounts of 19 amino acids in all groups, but only amino acids with significant differences are shown in Table 7. The fiber fractions affected the amino acids to a similar extent as the probiotic strain did, although they did not affect the same amino acids.

fed BSG than the other test diets, although no individual significances between rats fed the different fiber fractions could be seen.

Bacteriology

Figure 1:
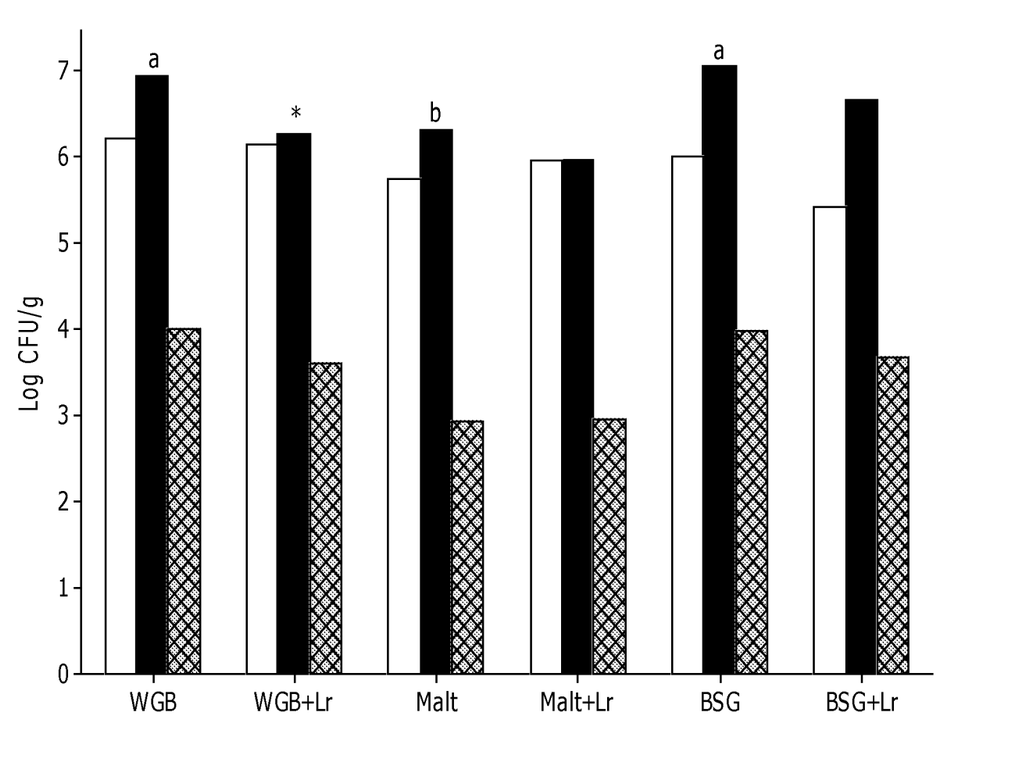
FIG. 1 shows the bacterial counts of *Lactobacillus* (white bars), *Bifidobacterium* (black bars) and Enterobacteriaceae (checked bars) in cecum content of rats fed whole grain barley (WGB), malt (Malt) or brewer's spent grain (BSG), and the same diets supplemented with *L. rhamnosus* (Lr). Values are means and those values of WGB, Malt and BSG, i.e. those without any added probiotics, with dissimilar superscript letters were significantly different, P<0.05. Mean values were significantly different from those for rats fed diets without bacteria, *P<0.05

In general, the viable cecal counts of bifidobacteria and Enterobacteiaceae were both affected by the fiber fractions and the bifidobacteria counts were also affected by *L. rhamnosus* (FIG. 1). Rats fed Malt had a lower count of bifidobacteria than rats given WGB or BSG (6.3±0.2 log CFU/g cecal content versus mean 7.0±0.1 log CFU/g cecal content, P<0.006), and when *L. rhamnosus* was added to the WGB diet the bifidobacteria counts were lower than in rats fed WGB only (6.3±0.2 log CFU/g cecal content versus 6.9±0.1 log CFU/g cecal content, P=0.021). Although the viable counts of Enterobacteriaceae in the Malt group were not significantly lower than in the WGB group, the p-value was very close to significance (P=0.059).

Butyric acid has been proposed to be important for colonic health, e.g. by reducing the risk of inflammatory bowel diseases and colon cancer. These effects may be due to its function as the main energy source of the epithelial cells, and its major role in regulation of cell proliferation and differentiation. Glutamine has been reported to also be a major energy source of mucosal epithelial cells, and as such able to recover and preserve the intestinal mucosa and prevent bacterial translocation. GBF, known to contain high amounts of β-glucans and glutamine, has been reported to reduce the epithelial inflammatory response both in subjects with ulcerative colitis and in mice with DSS-induced colitis. Pure barley β-glucans have previously been shown to give comparatively high amounts of butyric acid in rats, and glutamine in GBF has been suggested to be a substrate for the mucosa, since it is bound to the barley fiber. In this experiment, three different fractions of barley alone or in combination with a probiotic strain, *L. rhamnosus* were used to evaluate the potential role of brewer's spent grain (BSG) as a prebiotic product, regarding the cecal formation of CA,

|  |  |  |  |  |  |  | P-value | | |
|---|---|---|---|---|---|---|---|---|---|
|  | WGB | WGB + Lr | Malt | Ma + Lr | BSG | BSG + Lr | Fiber | Pro | Fiber × Pro |
| Serine, % | 6.3 ± 0.2 | 5.9 ± 0.2 | 6.2 ± 0.2 | 6.0 ± 0.2 | 7.0 ± 0.2 | 6.5 ± 0.3 | 0.008 | NS | NS |
| Glutamic acid, % | 2.7 ± 0.2 | 2.8 ± 0.1 | 2.6 ± 0.2 | 3.0 ± 0.3 | 2.5 ± 0.2 | 2.9 ± 0.1* | NS | 0.037 | NS |
| Glutamine, % | 14.0 ± 0.4$^a$ | 11.8 ± 0.3** | 11.6± 0.3$^b$ | 11.4 ± 0.6 | 12. ± 0.7$^{a,b}$ | 13.0 ± 0.7 | 0.030 | NS | NS |
| Tyrosine, % | 1.6 ± 0.1$^a$ | 1.6 ± 0.1 | 1.5 ± 0.0$^{a,b}$ | 1.6 ± 0.1 | 1.3 ± 0.1$^b$ | 1.6 ± 0.1* | NS | 0.038 | NS |
| Lysine, % | 11.3 ± 0.3$^{a,b}$ | 10.7 ± 0.5 | 10.4 ± 0.3$^a$ | 10.5 ± 0.3 | 11. ± 0.4$^b$ | 10.9 ± 0.6 | NS | NS | NS |
| Histidine, % | 1.9 ± 0.2$^a$ | 2.3 ± 0.2 | 2.3 ± 0.1$^{a,b}$ | 2.3 ± 0.1 | 2.6 ± 0.1$^b$ | 2.1 ± 0.2 | NS | NS | 0.024 |
| $NH_4$, % | 8.2 ± 0.3$^a$ | 10.7 ± 0.8* | 11.4 ± 0.9$^b$ | 12.5 ± 0.5 | 8.1 ± 0.2$^a$ | 10.1 ± 1.1 | 0.001 | 0.004 | NS |
| Total, mmol/L | 5.0 ± 0.5 | 5.6 ± 0.6 | 4.8 ± 0.5 | 4.3 ± 0.4 | 5.5 ± 0.6 | 5.4 ± 0.7 | NS | NS | NS |

[1]Values are means ± SEM, n = 7; Malt, Malt + Lr, n = 6; BSG, n = 5.
[2]Mean values of WGB, Malt and BSG, i.e. those without any added probiotics, with dissimilar superscript letters were significantly different (P < 0.05).
[3]Mean values were significantly different from those for rats fed diets without bacteria:
*P < 0.05,
**P < 0.01.

Rats given WGB had the highest proportion of glutamine (P=0.01 compared with the group given Malt) and tyrosine (P=0.027 compared with the group given BSG), while the proportion of histidine and $NH_4$ was lowest of the three fractions (P=0.01 compared with rats fed BSG, and P=0.01 compared with Malt and BSG, respectively). The proportion of glutamine and tyrosine was higher in the BSG+Lr group than in the BSG group (P=0.046 and P=0.025, respectively). Overall, the portal proportion of seronine was higher in rats levels of SCFA and amino acids in blood, and the cecal composition of the bacterial flora (lactobacilli, bifidobacteria, Enterobacteriacece) in rats compared with grain barley (WGB) and malt (Malt), and whether the supplementation of *L. rhamnosus* gave any additional effects.

Malt gave higher levels of butyric acid in the cecum, the distal part of the colon and the portal blood of rats compared with WGB, and in portal blood also compared with BSG. The propionic acid level was also higher in portal blood.

Increased circulating levels of both butyric and propionic acid have been associated with metabolic effects. Recently, it has been suggested that these acids may modulate proinflammatory markers and in that way affect parameters connected with metabolic disorders. An increased intake of dietary fiber from barley in the evening has also been reported to improve glucose tolerance at a subsequent standardized breakfast meal, which could be related to increased plasma levels of SCFA. It might be speculated whether the changed cecal microbiota in rats fed Malt facilitated the transportation of SCFA through the mucosa, compared with WBG and BSG. The importance of the composition of the microbiota, in this respect, is further established by the fact that the probiotic strain, *L. rhamnosus* 271, generally influenced the level and pattern of SCFA formed. Thus, the butyric acid levels in both cecum and portal blood were higher when the strain was added to the diets. Even though quite a few individual differences could be seen between the groups, especially in blood, the added probiotic clearly had an effect and increased the levels of SCFA, which was shown by the overall significance in Tables 4 and 5 (Pro). The p-value of the difference in butyric acid between Malt and Malt+FLr was very close to significance (P=0.055), and it may be speculated whether additional rats in the groups or an extended experimental period would have led to a significant difference. A higher level of SCFA in blood has been shown before when probiotics have been added to fiber-rich diets. However, it should be noted that the levels of especially butyric acid but also propionic acid in cecum and portal blood were considerably higher in rats fed the barley fractions compared with this earlier experiment in which rats were fed blueberry husks. The increased degree of fermentation was also reflected in the pH by probiotics and it was lower in those groups receiving *L. rhamnosus* 271. In this respect, it is worth mentioning that at low pH the growth of potential pathogens, such as Clostridia, is reduced, and thus it seems that *L. rhamnosus* 271 may counteract a pathogenic flora.

Rats fed Malt had the highest butyric acid level in the distal part of the colon (P<0.05 compared with WBG). It is of great importance that dietary fibers are able to reach not only the proximal colon but also the distal part, because colonic diseases such as ulcerative colitis and colonic cancer usually occur in this site of the colon. Subjects with ulcerative colitis increased their fecal levels of butyric acid after 4 weeks on a diet with β-glucan enriched oat bran, and unlike controls, complaints at entry were improved with this treatment. Similar results were obtained by Kanauchi and collaborators with germinated barley foodstuff.

The cecal pools and levels of CA were higher in rats fed Malt compared with WGB, indicating a high extent of fermentation of the fiber. However, the fiber, including the glucose containing dietary fiber polysaccharides, in malt was least fermented of the three barley fractions studied. A probable explanation could be that the fiber in whole grain barley is degraded during malting and not precipitated in ethanol during the dietary fiber analysis. This means that the dietary fiber intake for rats fed Malt in fact was higher than with the other barley preparations, leading to a higher formation of CA. Values in Table 2 are based on a fiber analysis, i.e. only polysaccharides having a higher degree of polymerization (around 20) are measured, resulting in an apparent lower degree of fermentation. However, this is not a problem with this method only, but with all currently used dietary fiber methodologies. Including indigestible carbohydrates of lower degree of polymerization in the calculation of fermentation will decrease the fecal excretion to approximately 36%. BSG was least fermented (P<0.05 compared with WGB), probably due to an enrichment of cellulose containing polysaccharides, known to be poorly fermented.

The number of bifidobacteria counts was lower with Malt than with the other barley fractions. Although the bacteria counted in this experiment does not make up for the whole microbiota, it may indicate that the microbiota was altered. A changed microbiota may also result in other pathways for fermentation and a changed formation of degradation products, as judged by the higher levels of butyric acid in the cecum and the distal part of colon in rats fed Malt compared with the other barley products.

The total content of protein, measured as amino acids, was nearly three times higher in brewer's spent grain than in malt and whole grain barley, while the composition of the protein was very similar in the three barley fractions. The contribution of protein from the barley fractions in the diets, however, was highest with Malt (Table 6). Nevertheless, there were no differences in total amount of amino acids in the portal blood. However, some differences were found in the distribution of the amino acids, and rats fed WGB had a higher proportion of glutamine in plasma than the group fed Malt. In this experiment, it was not determined whether whole grain barely contained indigestible protein, including glutamine, which could reach the colon for fermentation. It has been suggested that an increased formation of butyric acid may reduce the need for glutamine, thereby increasing the circulating glutamine levels. Malt giving high amounts of butyric acid did not show on any higher levels of glutamine in plasma of rats than the other barley fractions, indicating that glutamine does not reach the colon to any great extent and therefore is not absorbed there. In fact, blueberry husks in a diet containing casein as protein source have been shown to give similar plasma levels of glutamine as in this experiment, using the same animal model (data not published). This may imply that none of the barley fractions used in this experiment increased plasma levels of glutamine more than casein. The beneficial effects of GFB in man with ulcerative colitis and in rats with DSS-induced colitis have partly been ascribed to glutamine.

There are some difficulties when analyzing glutamine in the test materials. During acid hydrolysis glutamine is converted into glutamic acid, and the amount of glutamic acid therefore also includes the amount of glutamine. However, only traces of glutamic acid can be found in germinated barley foodstuff and consequently most of the measured amounts should be glutamine. Further, glutamine in barley has been reported to be bound to the dietary fiber, reaching the colon and after fiber fermentation being a substrate for the colonic mucosa. However, glutamine is known to be very fragile amino acid, and most of the glutamine not bound to the dietary fiber is degraded by gastric acid. The Malt group had lower plasma levels of glutamine, and it might be speculated whether this was connected to the malting process in some way. As discussed above, it seems as if the dietary fiber was degraded during malting, which may result in less amounts of bound glutamine.

The ammonia plasma level in the Malt group was higher than in rats fed WGB and BSG. The origin of ammonia in the portal vein is complex, but some arises from the metabolism of glutamine. This may be another reason for the lower proportion of glutamine in the Malt group. Previous studies in man have shown that an increased number of fecal bifidobacteria was associated with a reduced level of ammonia in feces and blood. *Bifidobacterium* spp. are known to use the ammonia as a nitrogen source for their growth. Rats fed Malt had a lower viable count of cecal bifidobacteria, indicating that this could explain the higher proportion of ammonia, found in the portal blood. Ammonia has been shown to be toxic to cells, and to alter synthesis of DNA, and thus has been proposed to be a promoter of carcinogenesis in humans. One way of decreasing the level of ammonia in rats fed Malt may be to add bifidobacteria. The *L. rhamnosus* used in this experiment did not decrease, but rather increased the level of ammonia in blood.

In conclusion, in the experiments performed in accordance with the present invention, barley in the form of whole grain barley, Brewers spent grain or malted barley in combination with a probiotic strain gave rise to a considerable increase in the formation of butyric acid in the colon, see table 4, and blood, see table 5, compared to the situation when the barley fractions were given by themselves. As can be seen in table 5, the increase is more than doubled for WGB and Malt, and almost doubled for BSG in blood. The commercial interest of a composition comprising these components is realized in view of the many beneficial effects connected with butyric acid. Thus, the formation of CA, not only butyric acid, increased when the probiotic strain *L. rhamnosus* was added to the barley fractions, though most effects were shown together with WBG, e.g. increased butyric acid levels in cecum and portal blood. In view of the similiarities of the cereals barley, oat and rye, it is expected that the same results will be obtained with the other cereals as well.

The invention claimed is:

1. A method of increasing formation of butyric acid in a subject's colon, the method comprising orally administering to the subject a non-fermented composition having an ability to increase the formation of butyric acid in the subject's colon,
   wherein the composition comprises at least one isolated probiotic strain of *Lactobacillus rhamnosus*,
   wherein at least 40% weight of the composition is at least one barley fraction selected from the group consisting of whole grain barley, malted barley, and brewer's spent grain, and
   wherein oral administration of the composition increases the formation of butyric acid in the subject's colon compared to oral administration of the same composition without the *Lactobacillus rhamnosus*.

2. The method according to claim 1, wherein the at least one isolated probiotic strain of *Lactobacillus rhamnosus* is *Lactobacillus rhamnosus* 271, DSM 6594.

3. The method according to claim 1, wherein the barley fraction has been milled, heat treated, extruded, expanded, drum-dried, flaked, or steam-cooked.

4. The method according to claim 3, wherein the barley fraction is additionally malted.

5. The method according to claim 1, wherein the barley fraction is a whole grain barley fraction.

6. The method according to claim 1, wherein the barley fraction is brewer's spent grain.

7. The method according to claim 1, wherein the barley fraction is provided as particles having a particle size in a range of approximately 0.1-10 mm.

8. The method according to claim 1, wherein the non-fermented composition is a medical food, a functional food, a dietary supplement, a nutritional product, a food, or a food additive.

9. The method according to claim 8, wherein the non-fermented composition is a food additive present in cereals, muesli, breads, biscuits, health bars, or spreads.

10. The method according to claim 8, wherein the non-fermented composition is a food, wherein the food is a drink, a beverage, a yogurt, a juice, or an ice cream.

11. The method according to claim 1, wherein the amount of *Lactobacillus rhamnosus* administered per day is $10^8$-$10^{12}$ colony forming units (CFU).

12. The method according to claim 11, wherein the amount of *Lactobacillus rhamnosus* administered per day is $10^9$-$10^{11}$ colony forming units (CFU).

13. The method according to claim 2, wherein the amount of *Lactobacillus rhamnosus* 271, DSM 6594, administered per day is $10^8$-$10^{12}$ colony forming units (CFU).

14. The method according to claim 13, wherein the amount of *Lactobacillus rhamnosus* 271, DSM 6594, administered per day is $10^9$-$10^{11}$ colony forming units (CFU).

15. The method according to claim 1, wherein the probiotic strain of *Lactobacillus rhamnosus* is freeze-dried.

16. The method according to claim 1, wherein orally administering the non-fermented composition improves a condition selected from the group consisting of metabolic syndrome, ulcerative colitis, Crohns disease, irritable bowel syndrome (IBS), and inflammatory bowel disease (IBD).

17. The method according to claim 1, wherein at least 50% weight of the composition is a barley fraction.

18. The method according to claim 17, wherein at least 65% weight of the composition is a barley fraction.

19. The method according to claim 18, wherein the composition consists of the at least one barley fraction and the at least one probiotic strain of *Lactobacillus rhamnosus*.

20. The method according to claim 1, wherein the amount of *Lactobacillus rhamnosus* administered per day is $10^6$-$10^{14}$ colony forming units (CFU).

21. The method according to claim 2, wherein the amount of *Lactobacillus rhamnosus* 271, DSM 6594, administered per day is $10^6$-$10^{14}$ colony forming units (CFU).

* * * * *